(12) United States Patent
Droll

(10) Patent No.: US 6,428,521 B1
(45) Date of Patent: Aug. 6, 2002

(54) FEMALE EXTERNAL CATHETER DEVICE

(76) Inventor: Kenneth R. Droll, 3870 N. Andrews Ave., #PH700, Fort Lauderdale, FL (US) 33309

(*) Notice: Subject to any disclaimer, the term of this patent is extended or adjusted under 35 U.S.C. 154(b) by 0 days.

(21) Appl. No.: 09/940,645

(22) Filed: Aug. 29, 2001

(51) Int. Cl.[7] .................................................. A61F 5/44
(52) U.S. Cl. ........................ 604/329; 604/331; 604/330
(58) Field of Search ............................... 604/327–331, 604/385.17

(56) References Cited

U.S. PATENT DOCUMENTS

| | | | |
|---|---|---|---|
| 3,683,914 A | * 8/1972 | Crowley | ................... 604/329 |
| 3,776,235 A | * 12/1973 | Ratcliffe et al. | ............. 4/144.3 |
| 3,995,329 A | 12/1976 | Williams | |
| 4,194,508 A | 3/1980 | Anderson | |
| 4,198,979 A | 4/1980 | Cooney et al. | |
| 4,421,511 A | 12/1983 | Steer et al. | |
| 4,563,183 A | 1/1986 | Barrodale et al. | |
| 4,615,692 A | 10/1986 | Giacalone et al. | |
| 4,681,572 A | 7/1987 | Tokarz et al. | |
| 4,799,928 A | 1/1989 | Crowley | |
| 4,889,532 A | * 12/1989 | Metz et al. | ................... 4/144.3 |
| 4,889,533 A | * 12/1989 | Beecher | ..................... 604/330 |
| 5,147,301 A | * 9/1992 | Ruvio | ........................ 600/29 |
| 6,183,454 B1 | * 2/2001 | Levine et al. | ................ 4/144.3 |

* cited by examiner

Primary Examiner—John G. Weiss
Assistant Examiner—C. Lynne Anderson
(74) Attorney, Agent, or Firm—M. K. Silverman

(57) ABSTRACT

A female external catheter device collects and then channels urine away from the human body to a collection drain. The device minimizes urinary track infections, nosocomial infections and reduces a patient's risk of infection complications. The device also reduces usage of indwelling urinary catheters. It is characterized by a ladle-like geometry in which the spoon thereof is an intra-labial collection cup and the handle is a hollow neck and nob that is secured within the vagina. Apertures with the nob enable venting of vaginal fluids thru a fluid egress channel.

10 Claims, 6 Drawing Sheets

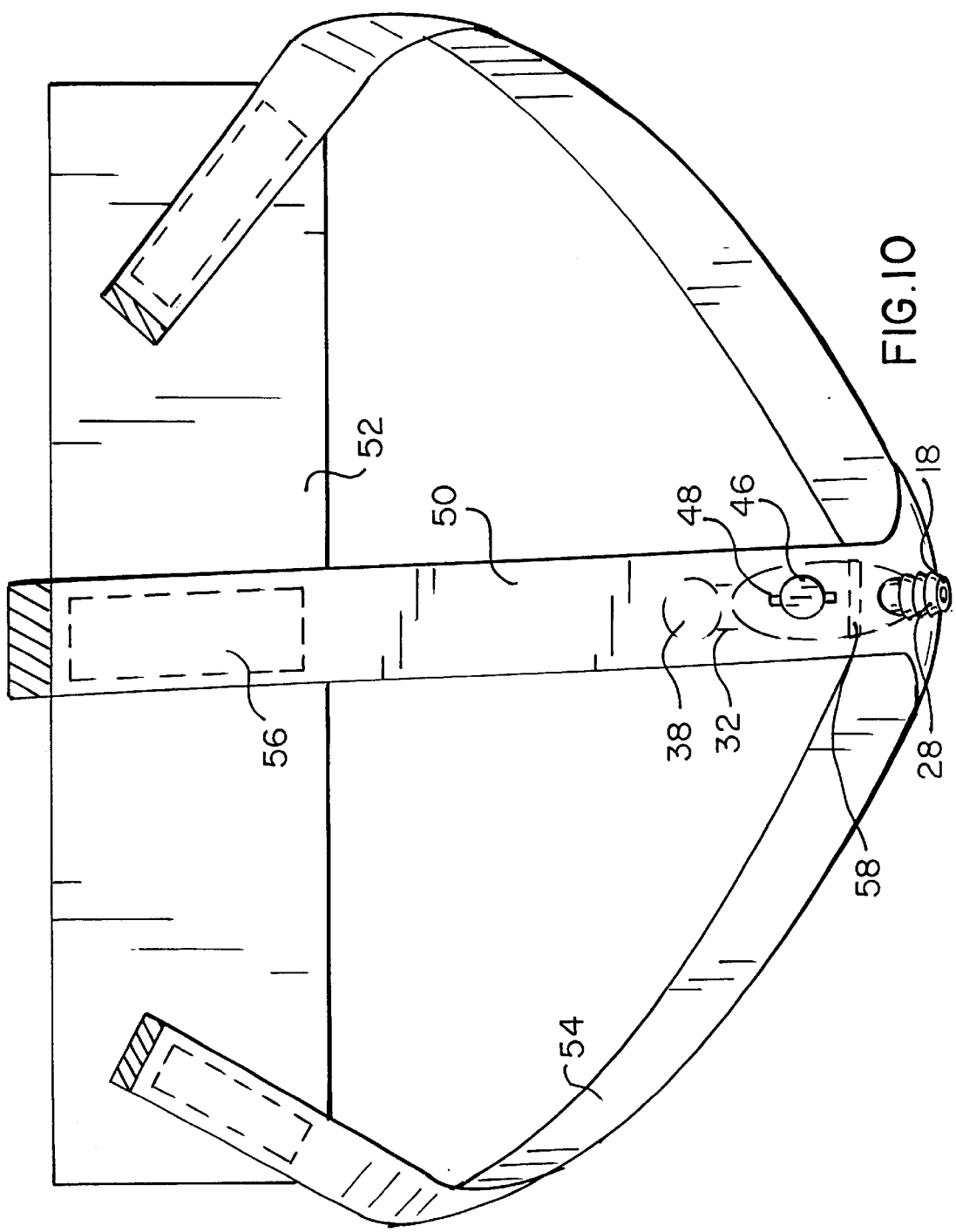

FEMALE EXTERNAL CATHETER DEVICE

BACKGROUND OF THE INVENTION

1. Field of the Invention

The present invention relates generally to urine collection devices and, more particularly, to a non-invasive female external urine collection device providing an input to an external catheter.

2. Description of the Prior Art

Hospitalized patients are often unable, and typically as a consequence of a post-operative condition, to control their urinary functions. Also, those who are able to control such functions may be physically unable to use a urinal or bedpan. Therefore, patients in either of said categories are fitted with urine collection devices known as catheters. Male patients are provided with internal or urethral catheters for as long as urine volumes need to be monitored, after which time, external catheters are used. Women, however, typically continue to keep internal catheters for as long as they remain unable to use normal facilities and, as a result thereof, frequently develop severe bladder or urinary track (UTI) infections. Such UTIs are typically nosocomial infections which, it has been determined, affect approximately five percent of all hospitalized individuals. For such patients, nosocomial infections can lead to pain, disability, a longer hospital stay, or worse. In the United States alone, the treatment of nosocomial infections add billions of dollars each year to the cost of healthcare. Further, it has been determined that UTIs account for forty percent of all nosocomial infections. Accordingly, the use of internal or indwelling urethral catheter account for a large proportion of all hospital-associated infections which occur. Since a nurse, or nursing assistant, typically does not have authority to determine whether or not a patient should use a urinary catheter, the issue then becomes one of which type of catheter can be used to minimize nosocomial and other urinary track infections. It has, thereby been determined that the instance of UTIs can be reduced where an external catheter can be used in lieu of an indwelling device. However, few such female external collection devices have appeared in the art, none of which have afforded an entirely satisfactory result.

Examples of such devices appear in U.S. Pat. No. 3,601,125 to Moss; U.S. Pat. No. 4,233,978 to Hickey; U.S. Pat. No. 4,563,183 to Barrodale; and U.S. Pat. No. 4,615,692 to Giacalone. Within this limited prior art, few patents suggest a unit having a projection or element adapted for insertion into the vagina itself, these comprising U.S. Pat. No. 3,776,235 to Ratcliffe; U.S. Pat. No. 4,194,308 to Anderson; U.S. Pat. No. 4,198,979 to Cooney; said U.S Pat. No. 4,563,183; and said U.S. Pat. No. 4,615,692.

In the case of said U.S Pat. Nos. 4,563,183 and 4,4,615,692, a flexible inflatable bladder is inserted into the vagina, thereby reducing the mechanical integrity of the entire structure. Another shortcoming of devices such as Ratcliffe and Anderson is that they provide or permit communication of some urine to the vagina which in itself, can increase the likelihood of infection, or are not anatomically compatible with the vagina. Other prior art tends to stretch or cause tissue damage in the area of the labia minora. Thus, there exists a continuing need for improved devices and methods for the drainage of urine from the urethra of women having little or no control of release of urine, this as a result of either a chronic or a particular post-operative condition. Such a device would, ideally, enable free movement of ambulatory women and, as well, reduce the chance of infection while improving the chance of a successful treatment of any infection that might occur. The requirements of an adequate female external catheter are therefore that of stability upon the person of the user and effective confinement of the expelled urine within a minimal area about the urethra to thereby minimize the possibility of communication of urine to other external female organs within the area of the urethra. These objectives, if achieved, will reduce the otherwise serious risk of infection of the bladder, urethra and/or vagina which, as above noted, has taken a serious role, particularly as a result of said nosocomial infections.

SUMMARY OF THE INVENTION

The instant invention relates to a female external catheter device, defined by a ladle-like body including a hollow elongate neck having a hollow bulbous nob integrally dependent from a distal end of said neck, an axis of elongation of said neck also defining a common axis of substantial radial symmetry of both said neck and nob. The device also includes an elongate hollow cup, integrally dependent from a proximal end of said neck, and having an axis of elongation generally normal to said neck axis, said cup defining a U-shaped cross-section within a plane transverse to a plane of symmetry of said device defined by said axes of elongation of said neck and said cup. Sidewalls of said cup are sized for intra-labial placement and, thereby, surround the urethral opening of a female user. Said cup also defines a transverse interior dimension in a range of about two to about four centimeters and a greatest linear dimension along said plane of symmetry of between about six and about ten centimeters. The device further includes a catheter drain nozzle including a central channel thereof in fluid communication with a channel of said neck and a lower interior surface of said cup. The fluid channel of said nozzle is, when in use, preferably in alignment with the gravity vector. Accordingly, said nob of said neck will upon insertion into the vaginal opening, comfortably and securely engage the inner sphincter muscles thereof, thus securing said device both within the vagina and upon the intra-labial region in a substantially fluid-tight manner. The apertured hollow nob and hollow neck of the device provide for proper fluid venting of the vagina, thus affording a channel of fluid discharge to the nozzle, and to eliminate urine backflow into the vagina.

It is therefore an object of the invention to provide a female external catheter device that overcomes the shortcomings of the prior art as set forth above.

It more specific is an object to provide a female external catheter means that provides for isolation of the urethral and vaginal openings, and which is invasive only as to the vagina for purposes of stabilization of the device, and fluid drainage of the vagina.

It is a further object of the invention to provide a female external catheter which provides for collection of substantially all urine passed by the patient but which minimizes the area of external female organs that are contacted by urine which is thereby collected.

It is a yet further object to provide a female external catheter device that can be effectively employed by walking, standing, seated, as well as reclining or prone patients, and which is of limited bulk to thereby enhance comfort to the patient. It is a still further object of the invention to provide a female external catheter device that is easy to apply and which, in many patients, may be self-applied.

It is a yet further object to provide such an external catheter device that is compatible with pre-existing drainage and collection means of types that are common in hospitals.

It is another object of the invention to provide a female external catheter device which will reduce the risk of urinary tract associated infections.

The above and yet other objects and advantages of the present invention will become apparent from the hereinafter set forth Brief Description of the Drawings, Detailed Description of the Invention and Claims appended herewith.

BRIEF DESCRIPTION OF THE DRAWINGS

FIG. 10 is a conceptual view of a harness assembly which may be employed in association with the inventive device to ensure the stability thereof on the body of the patient.

DETAILED DESCRIPTION OF THE INVENTION

Figure 1:
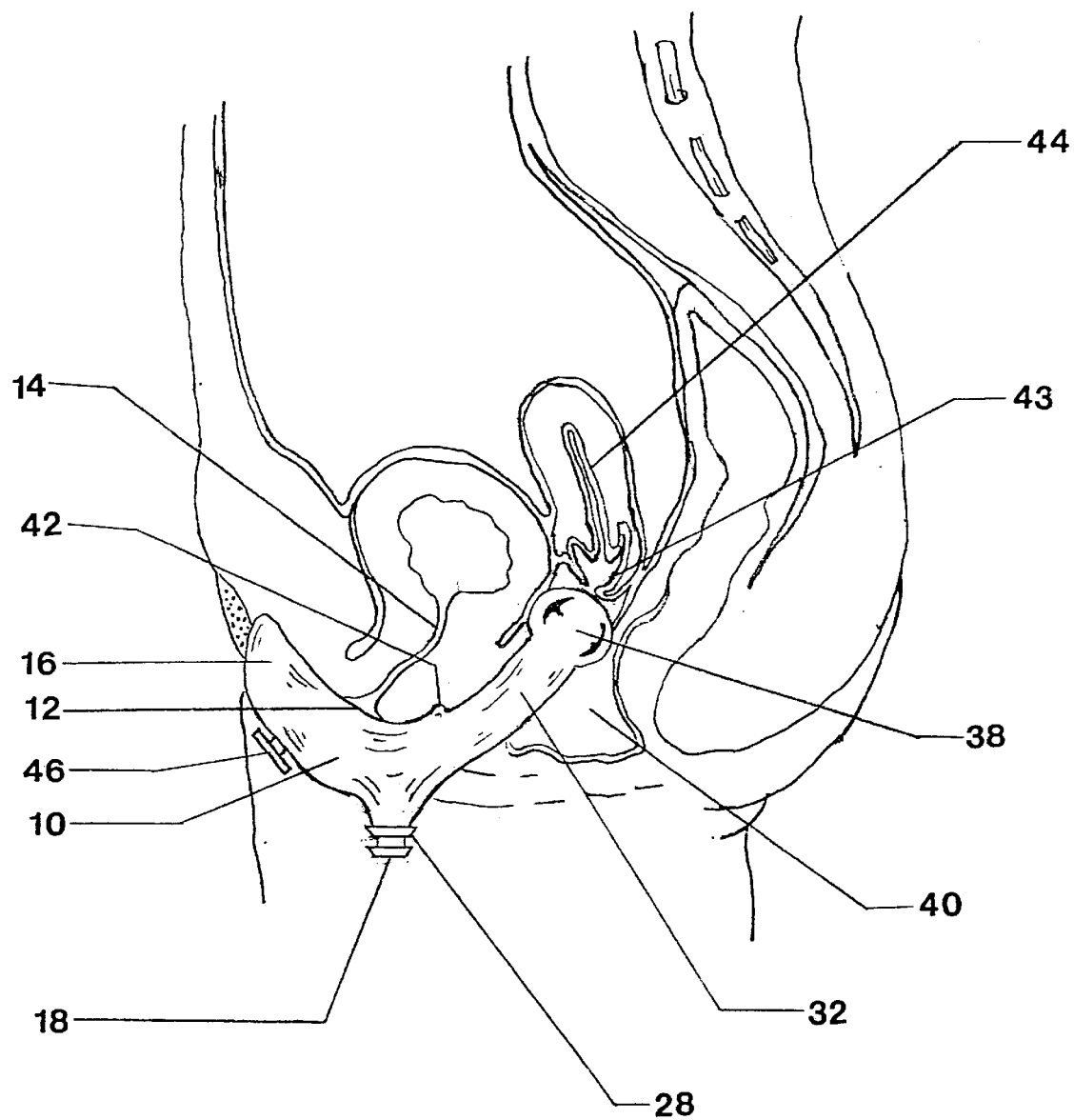
FIG. 1 is a cross-sectional anatomic view of an applicable portion of a female human body when the invention is in place.
Figure 2:
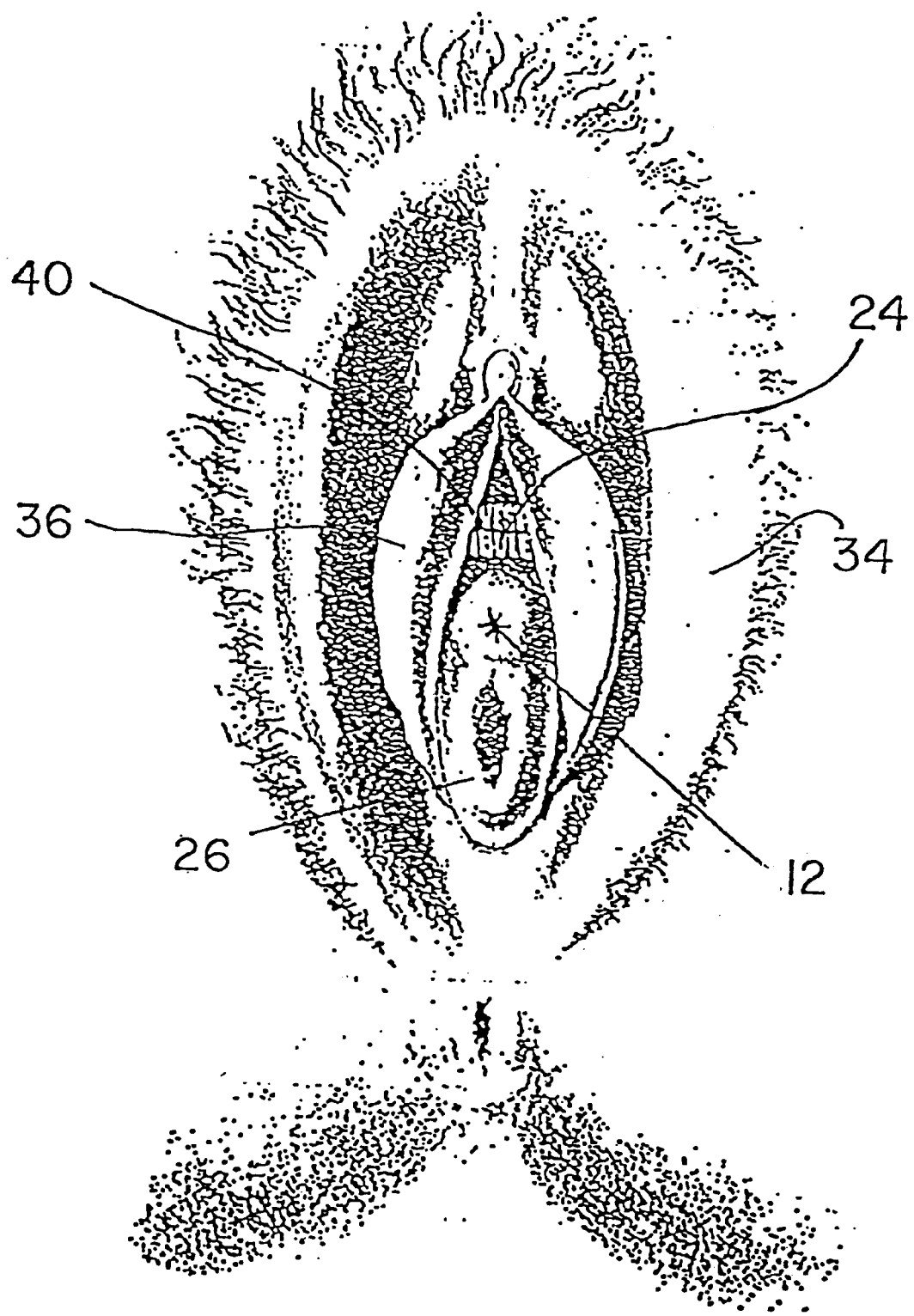
FIG. 2 is an anatomical view of the vulva inclusive of external female organs associated therewith.

With reference to the anatomical views of FIGS. 1 and 2, the orientation of the inventive female external catheter device 10 can more particularly be understood, as may be the basic female physiology with which the catheter cup must interface.

Therein, it is to be appreciated that the inventive device is one which is adapted to collect, and then channel away, urine from the human body to a drain tube and collection bag. Thereby, urine, after being expelled from the human body through orifice 12 of the urethra 14, will be gathered by cup 16 of device 10 (see FIGS. 3 to 9) and furnished to a drain tube to a fluid collection bag (not shown). Due to the diameter of drain channel 18, e.g., six to eight millimeters, there will occur minimal urine flow restriction thereby precluding any potential fluid back pressure in fluid cup 16 that might cause leakage at or about rim 22 of cup 16.

The half moon elongate shape of the cup 16 of the external catheter device is proportioned to accommodate the orifice 12 of the urethra 14 which, typically, is within vestibule 24 (see FIG. 2). However, in certain females, the location of the urethral orifice may vary such that, on occasion, the orifice of the urethra may be located near or even in the entrance of the vagina. (See FIG. 1.) Accordingly, the cup shaped geometry of the instant invention is adapted for compatibility with female physiology without regard to where the orifice of the urethra may be located. Further, in that the position of a patient requiring use of the external catheter device 10 may vary, on a patient-to-patient basis, the axis of output nozzle 28 may vary relative to an axis of elongation 30 of a neck 32 of the device. This is more particularly shown with reference to the views of FIGS. 3 and 4 in which, as may be noted, the axis or angulation of output nozzle 28 in the embodiment of FIG. 3 will differ from the angulation or axis of output nozzle 28A in the embodiment of FIG. 4 relative to neck axis 30 and axis of elongation 33 of cup 16, in the respective embodiments. Such different angulations of output nozzle 28 result from the fact that, to assure optimal functionality of the present invention, the output nozzle 28 must align with the gravity vector to the extent possible. Accordingly, a patient that spends most of her time in a sitting or partially sitting position will require a different embodiment of the invention than one lying substantially flat or prone after an operation or during convalescence.

Figure 3:
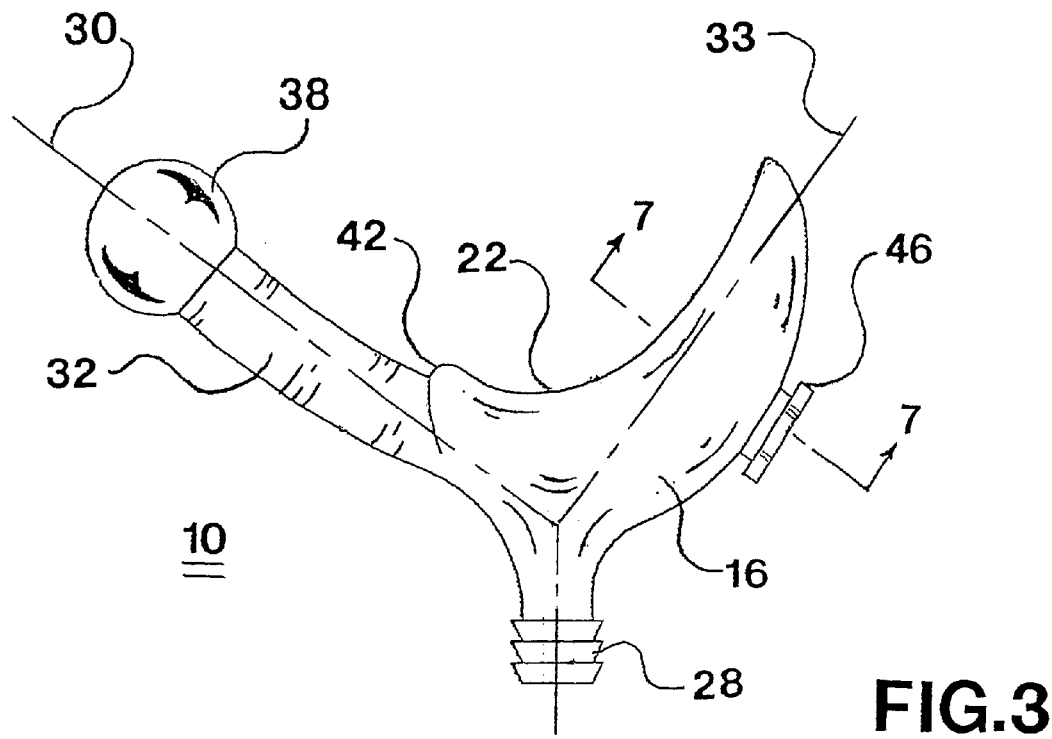
FIG. 3 and 4 are side elevational views of respective embodiments of inventive device showing alternative angulations of the axis of the output nozzle of the device.

It is noted that said axes 30 and 33 define a plane of symmetry of the device 10, and, in the embodiment of FIG. 3, output nozzle is about equiangular therebetweeen.

With respect to physiologic aspects of cup rim 22 of cup 16 within the patient, each side of said rim (see FIG. 7) will lie flat against the labium majus 34 (see FIG. 2), thereby engulfing nympha or labium minus 36 and thereby partially protruding into the orifice 26 of the vagina. This is more fully shown with reference to the physiological view of FIG. 1 in which shaft 32 as well as an integral nob 38 thereof will, in a woman of average size protrude approximately five centimeters thereinto, of which distance said nob 38 comprises about 1.5 centimeters. As may be noted in the views of FIGS. 3 and 4, nob 38 is circular in cross-section if viewed from axis 30 and through a plane transverse to said axis. In other words, the nob 38 is substantially spherical. The aggregate length of the nob and neck will typically fall within a range of 2 to 10 cm, and the diameter of said nob 1 to 3 cm.

The essential function of hollow neck 32 and hollow nob 38 is to assure a necessary level of stability of the device 10 relative to orifice 12 of the urethra, and venting of the vagina, thus affording a channel of fluid discharge to the nozzle, and to eliminate urine backflow into the vagina. It has, particularly, been found that through the use of nob 38, the diameter, at greatest dimension, thereof, which is about twice the width of neck 32 when measured transversely to its axis 30, will sufficiently engage the vagina to assure sufficient stability relative to urethral orifice 12 and urethra 14. More particularly, in a preferred embodiment, the vestibule 24 of the patient is desensitized so that that a smaller size catheter cup 16 may be used, thus enabling the cup's rim 22 to lay flat against inside edges 40 of vestibule area. See FIG. 2. Enabling nympha 36 to wrap around the exterior surface of the cup to thereby aid in holding the cup's position to ensure a fluid tight seal between cup edges 22 and nympha 36. Accordingly, it is to be appreciated that the combination of the particular transverse cross-section of cup 22, the length and geometry of neck 32 and its integral nob 38, all interact with external female organs to assure stability of the catheter cup relative thereto. It is of course to be appreciated that in addition to differences in directionality of the axis of output nozzle 28 relative to neck axis 30, the catheter cup itself will be made available in a variety of sizes depending upon the weight, size and physiology of a particular female patient. It is contemplated that five sizes will be available, each having the two output nozzle angulations shown in FIGS. 3 and 4, to substantially cover the universe of female patients.

Figure 5:
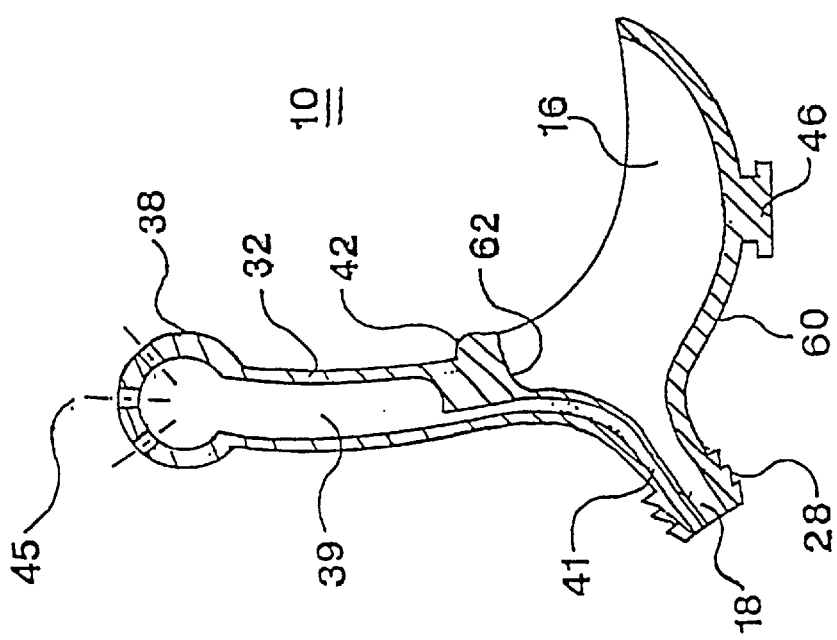
FIG. 5 is a cross-sectional side view of the device of FIG. 4 taken through the plane of symmetry thereof.

With reference to FIG. 5, the internal structure of the neck and nob may be more fully appreciated, that is, said elements exhibit a large internal cavity 39 which expends proximally downward to form a channel 41. Vaginal fluid inputs to this structure occur through apertures 45 of nob 38 but, however, may also be placed within the neck proper of the device. Said channel 41 also assures that urine from cup 16 can never backflow into the vagina.

It is to be further understood that the length of the nob and neck, as measured along neck axis 30 was determined by positioning nob 38 at exterior and interior sphincter vagina muscles 40 (see FIG. 1), but not past post anterior lip 43 of the vagina. Thereby, the sphincter muscles of a vagina aid in holding cup neck and nob thereby materially contributing to the stability of the catheter cup 16. As above noted, the neck 32 of the device is smaller in diameter than that of nob 38. It has been discovered that this geometry assures maximum beneficial use of sphincter muscles 40 in effecting a fluid tight seal around nob 38 which, thereby, improves the engagement of the nympha 36 about the exterior rim 22 of the cup 16.

Figure 6:
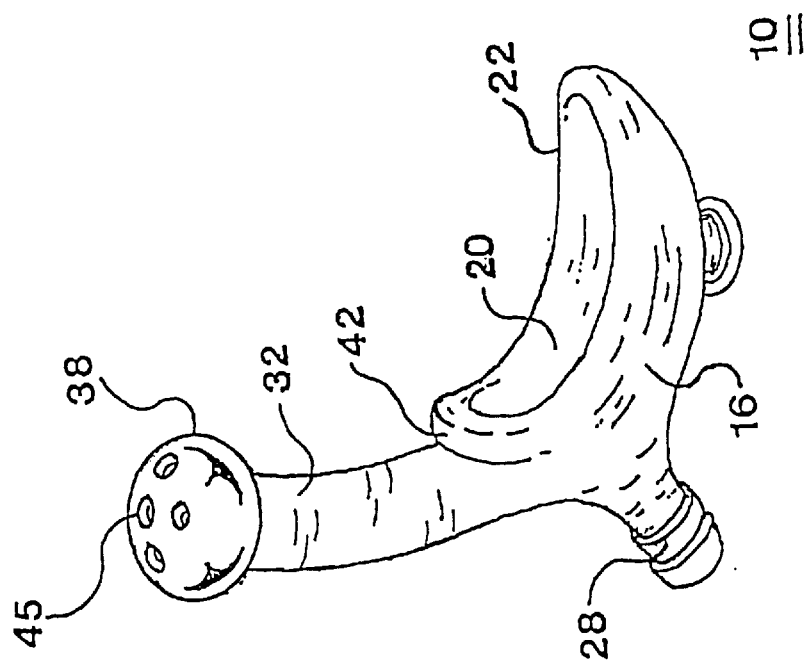
FIG. 6 is a perspective view taken of the device of FIGS. 4 and 5.
Figure 7:
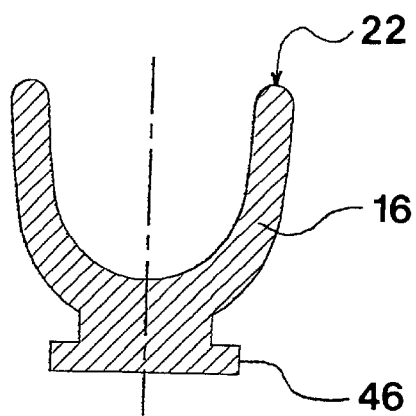
FIG. 7 is a cross-sectional view taken through Line 7—7 of FIG. 3.
Figure 8:
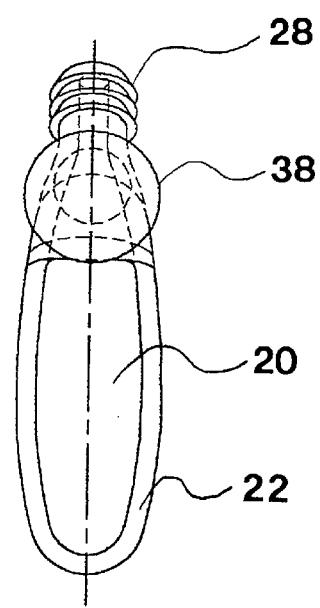
FIG. 8 is a top plan view of the inventive device.
Figure 9:
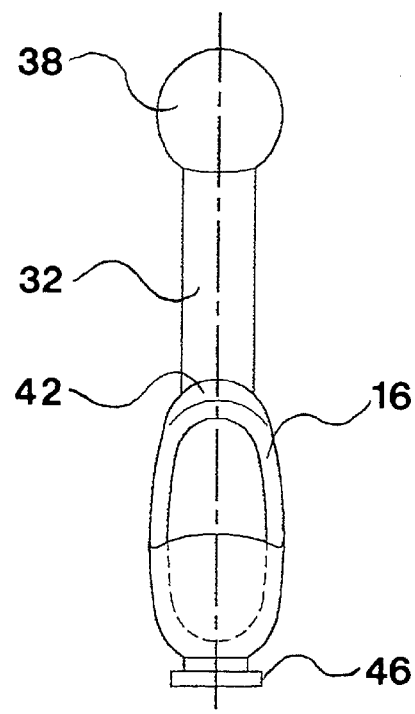
FIG. 9 is a front plan view thereof in which a harness button of the device defines the bottom of the device and the nob portion thereof defines the top thereof.

As may be noted with reference to FIGS. 6 and 7, edge 22 of the cup 16 should have sufficient width and curvature to assist in a fluid tight seal with the nympha and provide a comfortable fit to the body of the patient.

In the event that vestibule 24 is not desensitized, a larger cup size, or at least a larger cross-section of cup 16 of the device will be necessary to effect engagement of labium majus 34. The device size and use may range from that of an infant to a large adult.

Another distinguishing feature of the invention lies in transverse platform 42, the function of which is to assure that the neck and nob of the device is properly positioned within the vagina thereby precluding the possibly intrusion into, or damage to, uterus 44. (See FIG. 1)

Figure 4:
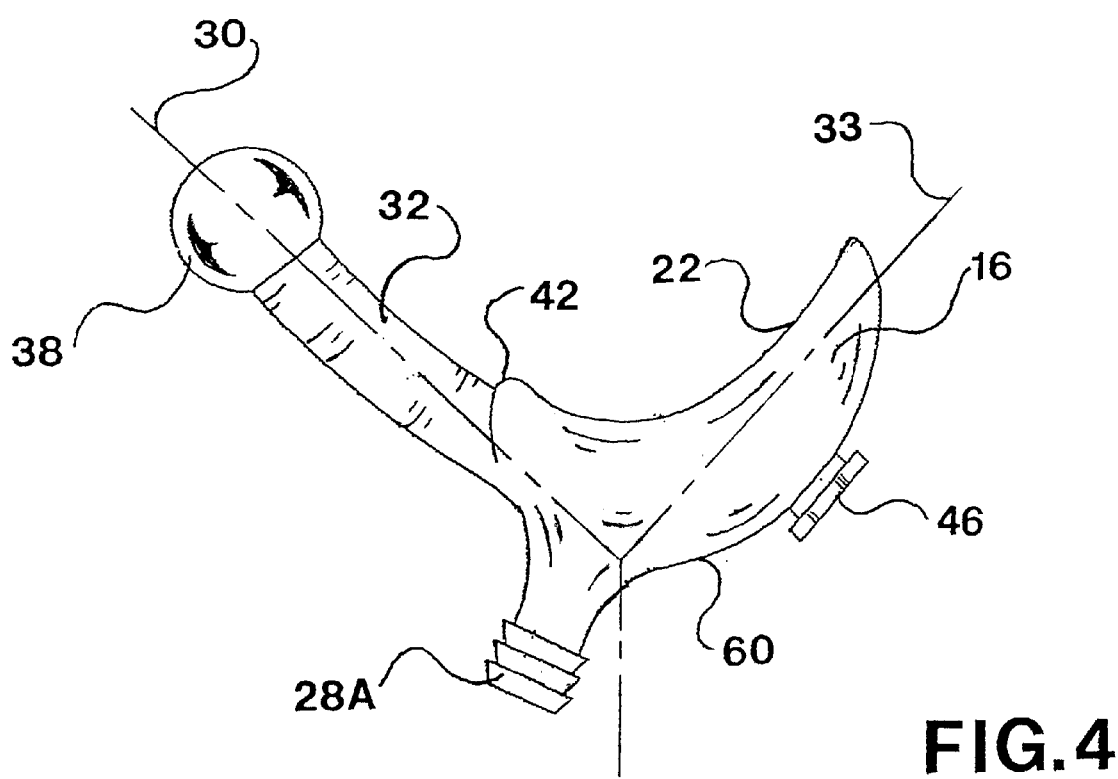

The internal extent of cup 16 relative to neck 32 may be appreciated with reference to FIG. 5 which shows that upper surface 62 of the cup extends in the direction of the neck and the nob to within about five millimeters of platform 42. It is to be also appreciated that the slight degree of curvature of neck 32 relative to the otherwise linear axis 30 shown in FIG. 4 is an essential aspect of the invention in that such curvature conforms to the natural slightly curved axis of the vagina.

The invention is further characterized by a button 46, the function of which is to facilitate securement of the device within slot 48 of a body harness 50 (see FIG. 10). As may be noted therein, said harness will typically include a waist portion 52, straps 54 and Velcro interfaces 56 by which adjustments in dimension to patients of varying sizes may be effected. Shown in phantom in FIG. 10 is nob and neck 38 and 32 respectively, as well as output nozzle 28 and its aperture 18. As may be noted, the exterior of nozzle 28 is provided with circumferential ridges sufficient to secure a drain tube thereto. Also, a thickness of cloth of about 13 millimeter or a double sided adhesive 58 may be provided at the internal interface between the bottom, shown as area 60 in FIG. 5, and the inside surface of the lower portion of the harness 50. Accordingly, by such by means, the inventive female external catheter device is stabilized relative to the patient.

In terms of materials of manufacture, there exist a variety of FDA grade plastics, surgical rubbers and silastics, such as silicones, which permit rim 22 and the neck and nob 32 and 38 respectively to be very soft and thereby sufficiently user friendly for purposes of the present application. In terms of weight, the catheter device will weigh in a range of 20 to 30 grams.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

I claim:

1. A female external catheter device in the nature of a ladle-like solid body, the device comprising:

(a) a hollow elongate neck having a hollow bulbous nob integrally dependent from a distal end thereof, an axis of elongation of said neck also defining a common axis of substantial radial symmetry of both said neck and nob, the interior of said neck and nob comprising a single internal cavity extending proximally downward to define a drain channel, said nob including apertures therethrough, (b) an elongate hollow cup, integrally dependent from a proximal end of said neck, said cup having an axis of elongation generally normal to said neck axis, said cup defining a U-shaped cross-section in a plane transverse to a plane of symmetry of said solid body defined by said axes of elongation of said cup and said neck, said sidewalls of said cup sized for intra-labial placement to thereby surround the urethral opening of a female user, said cup further having a transverse interior dimension in a range of about two to about four centimeters, and a greatest linear dimension along said plane of symmetry of about six to about ten centimeters; and (c) a drain output nozzle, including a central channel thereof, in fluid communication with a lower interior surface of said cup, which channel, during use by a patient, is preferably positioned in general alignment with the gravity vector, and said nozzle further includes a second channel comprising said drain channel of said internal cavity of said neck and nob, whereby said nob of said neck will, upon insertion into the vaginal opening, comfortably and securely engage the interior sphincter muscles thereof, thus securing said device within the vagina and the cup thereof in substantially fluid-tight communication with the intra-labial region, while permitting hygienic fluid venting of the vagina.

2. The device as recited in claim 1, in which an aggregate length of said neck and said nob comprises between about two and about ten centimeters.

3. The device as recited in claim 2, in which a diameter of said nob comprises a range of about one to about three centimeters.

4. The device as recited in claim 1, in which an axis defined by said channel of said nozzle is generally equiangular between said respective axes of elongation, and is upon said plane of symmetry of the device.

5. The device as recited in claim 1, in which a part of a base of said neck comprises a flat transverse surface defining means for defining the extent of insertion of said neck and nob of said device into the vagina, said surface situated upon said plane of symmetry of the device.

6. The device as recited in claim 5, further comprising:
   a harness button integrally dependent from a lower outer surface of, said cup, and upon said plane of symmetry of the device.

7. The device as recited in claim 5, in which said sidewalls of said cup define a width in a range of about three to about ten millimeters.

8. The device as recited in claim 5 in which said axis of said neck and nob of the device is slightly curved in the direction of said cup to thereby more closely conform to the natural physiology of the vagina.

9. The device as recited in claim 8 in which said device comprises an FDA grade polymeric material.

10. The device as recited in claim 6 further comprising:
    harness means proportioned for engagement of said button and nozzle of said device to thereby facilitate securement of the device within and upon the female patient.

* * * * *